US012582828B2

(12) United States Patent
Doerr et al.

(10) Patent No.: US 12,582,828 B2
(45) Date of Patent: Mar. 24, 2026

(54) PACING DEVICE AND METHOD OF OPERATION THEREOF

(71) Applicant: BIOTRONIK SE & Co. KG, Berlin (DE)

(72) Inventors: Thomas Doerr, Berlin (DE); Dirk Muessig, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 355 days.

(21) Appl. No.: 17/913,612

(22) PCT Filed: Mar. 17, 2021

(86) PCT No.: PCT/EP2021/056778
§ 371 (c)(1),
(2) Date: Sep. 22, 2022

(87) PCT Pub. No.: WO2021/191013
PCT Pub. Date: Sep. 30, 2021

(65) Prior Publication Data
US 2023/0146054 A1 May 11, 2023

Related U.S. Application Data

(60) Provisional application No. 62/993,082, filed on Mar. 23, 2020.

(30) Foreign Application Priority Data

Jun. 8, 2020 (EP) .................................... 20178713

(51) Int. Cl.
*A61N 1/39* (2006.01)

(52) U.S. Cl.
CPC ....... *A61N 1/39622* (2017.08); *A61N 1/3925* (2013.01); *A61N 1/3987* (2013.01)

(58) Field of Classification Search
CPC .............. A61N 1/3756; A61N 1/37564; A61N 1/39622
See application file for complete search history.

(56) References Cited

U.S. PATENT DOCUMENTS 7,603,172 B2   10/2009  Lian et al.
8,046,069 B2   10/2011  Kramer et al.
(Continued)

OTHER PUBLICATIONS

International Search Report (PCT/ISA/210) and Written Opinion (PCT/ISA/237) mailed on Jun. 9, 2021, by the European Patent Office as the International Searching Authority for International Application No. PCT/EP2021/056778.

*Primary Examiner* — Eric D. Bertram
(74) *Attorney, Agent, or Firm* — Buchanan Ingersoll & Rooney PC

(57) ABSTRACT
A pacing device, a system comprising the pacing device and a method for operation of the pacing device, wherein the pacing device comprises a housing, a processor and a receiver electrically connected to the processor, wherein the processor is adapted to
  deliver signals for electric stimulation of a patient's heart according to at least one first stimulation mode and
  deliver signals for electric stimulation of the patient's heart according to an antitachycardiac pacing mode (ATP mode), wherein the ATP mode is initially deactivated and/or is to be upgraded,
wherein the receiver is adapted to receive an ATP confirmation signal transmitted by an external device or produced by operation of an actuator accommodated at the housing of the pacing device,
wherein the processor is adapted to upgrade the ATP mode and/or to activate the ATP mode only if the ATP confirmation signal comprises a pre-defined confirmation information.

14 Claims, 6 Drawing Sheets

(56)                References Cited

U.S. PATENT DOCUMENTS

|  |  |  |  |  |
|---|---|---|---|---|
| 8,744,572 | B1 * | 6/2014 | Greenhut | A61N 1/3621 607/4 |
| 10,265,534 | B2 * | 4/2019 | Greenhut | A61N 1/3621 |
| 11,235,163 | B2 * | 2/2022 | Huelskamp | A61B 5/686 |
| 2006/0247700 | A1 | 11/2006 | Jackson |  |
| 2007/0191894 | A1 * | 8/2007 | Li | A61N 1/3621 607/14 |
| 2009/0163966 | A1 * | 6/2009 | Perschbacher | A61N 1/3621 607/4 |
| 2017/0043174 | A1 * | 2/2017 | Greenhut | A61N 1/3987 |
| 2018/0243578 | A1 * | 8/2018 | Volosin | A61N 1/3987 |
| 2019/0160285 | A1 * | 5/2019 | Huelskamp | A61N 1/3622 |

* cited by examiner

WARNING:

The ATP mode is only allowed to be activated, if a defibrillator is implanted and activated. A defibrillator is implanted and activated?

No    Yes

WARNING:

Are you sure you want to activate the ATP-Function?

No    Yes

PACING DEVICE AND METHOD OF OPERATION THEREOF

CROSS-REFERENCE TO RELATED APPLICATIONS

This application is the United States National Phase under 35 U.S.C. § 371 of PCT International Patent Application No. PCT/EP2021/056778, filed on Mar. 17, 2021, which claims the benefit of European Patent Application No. 20178713.2, filed on Jun. 8, 2020 and U.S. Provisional Patent Application No. 62/993,082, filed on Mar. 23, 2020, the disclosures of which are hereby incorporated by reference herein in their entireties.

TECHNICAL FIELD

The present invention is generally directed to a pacing device, for example, an implantable leadless pacemaker, with a housing, wherein the pacing device comprises a processor and a receiver electrically connected to the processor or integrated therein, wherein the processor is adapted to deliver signals for electric stimulation of a patient's heart according to at least one first stimulation mode. The present invention is further directed to a method for operation of a pacing device.

BACKGROUND

Implantable stimulation devices such as pacing devices (e.g., implantable cardiac pacemakers or implantable leadless pacemakers) are well known medical devices that allow stimulation of the heart of a patient. In general, those medical devices are battery operated and a stimulation component is directly implanted into the heart's ventricle or atrium. Implantable cardiac pacemakers have at least an elongated stimulation lead which reaches from the device housing into a heart chamber where it is anchored. ILPs are miniaturized pacing devices which are entirely implanted into the heart chamber.

Implantable stimulation devices with a defibrillation function are known in the art, as for instance implantable cardioverter-defibrillators (ICD) or subcutaneous implantable cardioverter-defibrillators (SICD). Such devices typically comprise of a device housing and at least one elongated stimulation lead which extends from the housing. The housing of an ICD is typically implanted in a skin pocket below the clavicle, wherein the stimulation lead reaches into the ventricle of the heart where it is fixed. The housing and stimulation lead of an SICD are implanted under the skin (i.e., subcutaneously), in a way that a shock vector that runs through the cardiac ventricles is created between the stimulation electrode(s) of the lead and the SICD housing.

The medical device is chosen according to the patient's cardiac condition, i.e., the required cardiac therapy.

Implantable pacemakers or ILPs are used for patients who suffer from a bradycardia, that is if a heart that beats too slow to fulfil the physiological needs of the patient. The implantable pacemaker or ILP applies electrical stimulation to the heart in order to generate a physiologically appropriate heartrate.

ICDs are used for patients who suffer from ventricular tachycardia and fibrillations. The ICD is able to apply antitachycardia pacing (ATP) therapy (i.e., pacing the heart with a faster stimulation rate than the tachycardia rate) to terminate a tachycardia, or a shock therapy (i.e., high energetic electric shock which is applied to the ventricles to terminate the tachycardia to bring back the heart to a physiological rhythm) if the tachycardia persists after ATP attempts.

SICDs are configured to deliver a shock therapy, but no pacing therapy or ATP therapy. That is due to the distance between stimulation lead and the cardiac chambers, so that a low energetic stimulation pulse could not be delivered effectively to a cardiac pacing site.

An ILP may deliver pacing therapy and ATP, but no shock therapy. Due to the highly restricted device size, it has a small battery capacity and lack of space for charging capacitors required for providing a shock therapy.

Moreover, implantable leads pose a risk to the patient and can therefore be a problem. The lead is an elongated insulated electrode wire which reaches from the device housing into the venous system of the heart where it is anchored in the ventricle. It undergoes different forces and movements with every beat of the heart, which can result in lead dislodgement, insulation failures and lead breach. That problem does not occur with SICDs and ILPs, because these devices have no intracardiac elongated lead. Especially for patients who have no adequate vascular access or are at high risk for infection, no elongated leads can be implanted inside the heart.

However, there are circumstances in which a patient suffers from various cardiac arrhythmias that require different cardiac therapies. In such cases, a system of implantable devices may be implanted comprising at least two medical devices or units.

Furthermore, there exist cardiac arrhythmias for which different therapies are suitable and one treatment is more favorable, e.g., more comfortable, for the patient. Further, some therapies may cause another arrhythmia, so that an additional therapy is required in order to stop this arrhythmia. In practice, ventricular tachycardia, for example, may be treated using ATP therapy or shock therapy, wherein shock therapy is often uncomfortable for patients as the shocks are emitted unexpectedly and may be painful. In addition, shock therapies cause a considerable decrease in the longevity of the battery. Nevertheless, shock therapy is inevitable if a ventricular tachycardia leads to ventricular fibrillation as ATP therapy is not suitable to treat fibrillations.

For instance, a patient who has a contraindication for intracardiac elongated leads and who suffers from ventricular tachycardia requires pacing therapy, ATP and shock therapy. In such case, a system of implantable medical devices may be implanted comprising at least a first implantable stimulation device and a second implantable stimulation device, wherein the first implantable stimulation device may be an ILP, and the second device an SICD.

Cardiac rhythm management systems comprising multiple treatment therapies are, for example, provided by a combination of S-ICD and ILP as disclosed in the prior art documents U.S. Publication No. 2019/0160285 A1 and U.S. Pat. No. 10,265,534 B2. The coordination of the elements of such systems is obligatory in order to provide proper treatment as the therapies may be ineffective if they are applied simultaneously.

However, an external or internal communication within a system comprising at least two medical devices, i.e., between one implanted medical device and an external device or between two implanted medical devices, has some disadvantages. These disadvantages are mainly due to the fact that the communication requires communication interfaces, which in turn cause increased energy consumption. In addition, the communication interfaces are vulnerable for cyber-attacks. Furthermore, an undisturbed communication channel is required in order to provide a reliably functioning of such system.

In view of the above facts, there are multiple advantages using a combined system of pacing devices. Nevertheless, such system requires structured rules for communication and cooperation between the members of the system to function properly and requires reliable and a respective adaption of the pacing device if it is part of a system comprising several medical devices.

The present disclosure is directed toward overcoming one or more of the above-mentioned problems, though not necessarily limited to embodiments that do.

SUMMARY

It is an object of the present invention to provide an implantable pacing device and method to operate a pacing device which provides reliable stimulation therapy against tachycardias, e.g., in the combination of ATP therapy and shock delivery.

Therefore, it is an object of the present invention to provide a pacing device which can be used individually or in a system of two or more medical devices. It is a further object to define an operation method for such pacing device.

At least the above problems are solved by an implantable pacing device, for example, an implantable leadless pacemaker, with a housing, wherein the pacing device comprises a processor and a receiver electrically connected to the processor or integrated therein, wherein the processor is adapted to deliver signals for electric stimulation of a patient's heart according to at least one first stimulation mode. The pacing device is further adapted to deliver signals for electric stimulation of the patient's heart according to an anti-tachycardiac pacing mode (ATP mode), wherein the ATP mode is initially deactivated and/or is to be upgraded, wherein the receiver is adapted to receive an ATP confirmation signal transmitted by an external device or produced by operation of an actuator accommodated at the housing of the pacing device, wherein the processor is adapted to upgrade the ATP mode and/or to activate the ATP mode in order to be used in cooperation with another medical device, for example, a defibrillation device, only if the ATP confirmation signal comprises a pre-defined confirmation information. In one embodiment the pre-defined confirmation information may contain the information that The above defined inventive pacing device can be used individually as well as in a system of two or more medical devices. Together with the defibrillation device the ATP mode of the pacing device can be used if the usage is confirmed by an operator or the patient. As is indicated above, if an ATP mode is existent (i.e., initially contained in the pacing device or upgraded) and activated, ATP therapy is delivered by the pacing device, preferably in coordination with a treatment by the defibrillation device because a ventricular tachycardia may lead to ventricular fibrillation for which ATP therapy is not suitable. Fibrillations may be treated by a shock therapy provided by the defibrillation device.

In connection with the above invention, both medical devices, i.e., pacing and defibrillation devices, may be implanted in the chest cavity. More precise, the pacing device may be implanted in one heart ventricle or atrium and the defibrillation device may be implanted outside the heart. Further, the at least one pacing device comprises a detection unit, e.g., comprising one or more electrodes adapted to be implanted into the heart's tissue, adapted to detect a patient's cardiac rhythm and a processor adapted to analyze the detected patient's cardiac rhythm and to deliver signals for a first antitachycardia pacing (ATP) therapy if activated and/or if the ATP therapy mode is upgraded. The pacing device with the detection unit and the processor may be formed as an integral structure.

Furthermore, the at least one defibrillation device may comprise a second detection unit, wherein the second detection unit may be adapted to detect the patient's cardiac rhythm, and the second processor may be adapted to analyze the detected patient's cardiac rhythm and to deliver signals for shock therapy or a second anti-tachycardia pacing (ATP) therapy only if, if applicable, a first anti-tachycardia pacing therapy provided by the pacing device is absent. In case that the defibrillation device is an S-ICD, the second detection unit may comprise at least one detection electrode to detect the patient's cardiac rhythm and the second processor may be electrically connected to at least one shock coil and/or a pulse generator via an electrode lead. The electrode lead may be fixed to the pulse generator or may be connected via a connector pin. Further, the S-ICD may be implanted completely subcutaneous, wherein the components are positioned around the heart but not within the heart. The shock coil and a housing of the S-ICD are accommodated such that an electric shock wave produced by the shock coil is transmitted via at least one heart ventricle to the electrically conducting housing of the S-ICD. As there are no components of the S-ICD directly inserted into the heart, the advantages of an S-ICD are consequently a less irritation of the heart, a lower risk of infection and less mechanical stress of the components. The S-ICD may be placed according to anatomical guidance and does not require any imaging systems such as an X-ray imaging system. The electrode lead of the S-ICD may be inserted parallel to the sternum and the housing with the pulse generator and the second processor may be placed at the left chest wall.

If the ATP mode is upgraded and/or activated, an ATP therapy triggered by respective signals produced by the processor of the pacing device may be delivered by the pacing device. The ATP therapy may be delivered by the pacing device if the analysis of the patient's cardiac rhythm within a pre-defined preceding first time period reveals a pre-defined first tachycardia criterion. The ATP therapy is triggered by the respective signals of the processor and provided by a respective ATP signal generator of the pacing device which is connected to the processor and produces the signals which are to be sent by a subset of at least two electrodes to the heart of the patient. Alternatively or additionally, an ATP therapy or shock therapy triggered by the respective signals produced by the second processor of the defibrillation device is only allowed to be delivered if some pre-defined conditions are satisfied. In particular, if the analysis of the patient's cardiac rhythm within a pre-defined preceding second time period reveals a pre-defined second tachycardia criterion, and if applicable, an absence of a antitachycardia pacing therapy provided by the pacing device. The ATP therapy or shock therapy is provided by a respective signal generator of the defibrillation device which is connected to the second processor and produces signals to be sent by a subset of at least two electrodes connected to the housing of the defibrillation device to the heart of the patient. The shock therapy may be provided by a shock unit of the defibrillation device which is connected to the second processor and produces at least one shock signal via at least one shock coil connected by a lead to the housing of the defibrillation device.

According to one embodiment, the processor of the pacing device may adapted to allow delivery of signals for ATP therapy only if the analysis of the patient's cardiac rhythm within a pre-defined preceding first time period reveals a pre-defined first tachycardia criterion and an absence of a shock therapy of the defibrillation device.

The existence of a pre-defined first tachycardia criterion or second tachycardia criterion may be revealed if, for example, a pre-defined heart rate or QRS duration is exceeded by the is detected cardiac rhythm of the patient within the first time period or the second time period. Therefore, the first and second processors may be adapted to analyze the detected patient's cardiac rhythm, wherein the detected patient's cardiac rhythm may be realized by a sensed electrocardiogram (ECG). For example, the pre-defined heart rate up to which an ATP-therapy is delivered may be 120 to 180 bpm (beats per minute). This criterion may be part of the first tachycardia criterion. Moreover, shock therapy may be delivered when the heart rate is above 180 to 220 bpm.

The first time period or the second time period may be regarded as, for example, 5 to 10, 15, 20, 25, 30, 35, 40, 45, 50, 55 to 60 seconds, or 1, 1.5, 2, 2.5, 3, 3.5, 4, 5 minutes in the past from the actual/most recent time point. The first and the second time period may be different in length, for example, the first time period is longer than the second time period.

The existence or absence of the shock therapy provided by the defibrillator device may be revealed by the processor by the analysis of the detected patient's cardiac rhythm, as well, wherein the detected patient's cardiac rhythm may be given by a sensed ECG. Moreover, the detection of an applied shock therapy can be based on the detection of the high voltage applied and optional based on the detection of the typical shock waveform (e.g., biphasic waveform). The decision whether a shock is applied is made by the first processor, for example, by a detailed analysis of the ECG signals with regard to the peak height, the peak width and the peak distribution over time. If in the ECG no shock signal is detected within the first time period, the result of the first processor's analysis of the ECG signal is that no shock therapy was provided by the defibrillator device during the first time period.

Further, the existence or absence of the ATP therapy provided by the pacing device may be revealed by second processor by the analysis of the detected patient's cardiac rhythm, as well, wherein the detected patient's cardiac rhythm may be given by a sensed ECG. For instance, the detection of an ATP delivery could be based on the recognition of the typical ATP pattern (5-10 pacing pulses with a constant interval [Burst] or a decreasing interval length for per inter-pulse interval [Ramp]). The decision whether a shock is applied is made by the second processor, for example, by a detailed analysis of the ECG signals with regard to the peak height, the peak width and the peak distribution over time. If in the ECG no ATP therapy signal is detected within the second time period, the result of the second processor's analysis of the ECG signal is that no ATP therapy was provided by the pacing device during the second time period.

The pacing device and the defibrillation device of the system use the electrical signals of the respective other device in order to detect whether there was a therapy provided by the other device within a respective pre-defined time period prior the actual/recent time point. Additional communication between the devices, for example, using radio waves or other communication channel is not necessary. Accordingly, no additional communication unit/interface or no energy consumption for separate communication or for keeping a communication unit active is necessary. The coordination/management of the therapy of the at least two devices works by using the electrical signals produced by the respective patient or of an implanted device for the therapy of the same patient. Relevant electrical signals are for instance pacing pulses (amplitudes between 0.2 to 10V, pulse width 0.1 to 1.5 ms), and defibrillations shocks (monophasic or biphasic waveform; 100 to 1400V; pulse duration 4 to 80 ms). Further, the usage of the inventive system is user friendly as well as simple and cost-effective in its structure.

Some communication to the external device (e.g., a computer) is only needed for activation or upgrading of the pacing device by the ATP mode. This communication may be reduced to the initialization of the pacing device or any pre-defined or activated service date. Additionally, the receiver and the communication are only necessary in connection with the pacing device and not for the defibrillation device. The external device may comprise a display showing a predefined information regarding the upgrade or the activation of the ATP mode, for example, containing additional notes, such as warning notes, or references to notes contained in at least one document accompanying the pacing device, on the necessary simultaneous implantation of a defibrillation device such as an S-ICD. If the user provides its confirmation and indicates that the ATP mode shall be upgraded or activated, a respective pre-defined confirmation signal is transmitted to the receiver and afterwards to the processor of the pacing device. The confirmation signal may contain the date of confirmation, the time of the day and/or a confirmation code and/or specific parameter settings for ATP delivery (e.g., specific ATP mode, cycle length, pacing amplitude, pulse duration, etc.). Alternatively, the confirmation signal may be produced by operation of an actuator accommodated at the housing of the pacing device, for example, a switch, prior or during implantation of the pacing device. A second confirmation may be demanded from the operator/patient before the respective pre-defined confirmation signal is transmitted to the receiver of the pacing device.

In one embodiment, the pacing device further comprises a transmitter which may be separate from the receiver or integrated, thereby forming a transceiver, wherein the processor is adapted to provide pre-defined warning information data comprising warning information about the usage of the ATP mode, wherein the transmitter is adapted to transmit the warning information data to an external device. It may be useful if the receiver is adapted to receive the pre-defined ATP confirmation signal in response to the transmitted warning information data.

In one embodiment, the receiver or transceiver of the pacing device is adapted to receive the ATP confirmation signal and/or the upgrade information for the ATP mode wirelessly, for example, using near field communication or Bluetooth™, or via a telecommunication channel using, e.g., 4G, 5G, UMTS or GSM, or via a lead electrically connected to the pacing device.

In one embodiment, the receiver of the pacing device is adapted to receive the ATP confirmation signal prior, during or after implantation of the pacing device.

In one embodiment, the pre-defined confirmation information may comprise additionally at least one parameter of an additional anti-tachycardia device type, for example, of a defibrillator type, wherein the pacing device and the additional anti-tachycardia device are adapted to be implanted into the same patient so that the processor of the pacing device is adapted to the signals receivable from the additional antitachycardia device, in particular regarding the analysis of the detected heart rhythm signals.

In one embodiment, the processor is adapted to apply at least one criterion for ventricular/supraventricular tachycardia discrimination with regard to a cardiac rhythm detected by a detection unit of the pacing device.

In one embodiment, the ATP mode comprises at least two different antitachycardia pacing pattern elements usable during electric stimulation of the patient's heart according to the ATP mode.

Moreover, the ATP therapy delivered by a respective impulse generator of the pacing device and/or the defibrillation device may comprise pattern elements, for example, bursts, ramps and/or bursts with an extra stimulus, wherein preferably the number of pattern elements may be at least 5, preferably at least 8. Thereby the ATP therapy may better be adapted to the patient's needs.

In one embodiment, a first antitachycardia pacing pattern element comprising at least one burst and/or a second antitachycardia pacing pattern element comprising at least one ramp and/or a third antitachycardia pacing pattern element comprising at least one burst in combination with an extra stimulus.

At least the above problem is further solved by a heart treatment system comprising the above defined pacing device and an additional antitachycardia device, for example, a subcutaneous implantable cardioverter defibrillator (S-ICD).

Further, the above mentioned limitations and further explanations of the system do also apply to the embodiments of the method described below.

At least the above problem is further solved by a method for operation of an implantable pacing device, for example, an implantable leadless pacemaker, with a housing, wherein the pacing device comprises a processor and a receiver electrically connected to the processor or integrated therein, wherein the processor is adapted to deliver signals for electric stimulation of a patient's heart according to at least one first stimulation mode. The processor is further adapted to deliver signals for electric stimulation of the patient's heart according to an antitachycardiac pacing mode (ATP mode), wherein the ATP mode is initially deactivated and/or is to be upgraded, wherein the receiver receives an ATP confirmation signal transmitted by an external device or by produced by operation of an actuator accommodated at the housing of the pacing device, wherein the processor upgrades the ATP mode and/or activates the ATP mode only if the received ATP confirmation signal comprises a predefined confirmation information.

In one embodiment of the method, the pacing device further comprises a transmitter, wherein the processor is adapted to provide pre-defined warning information data comprising warning information about the usage of the ATP mode, wherein the transmitter transmits the warning information data to an external device. The receiver may receive the ATP confirmation signal in response to the transmitted warning information data.

In one embodiment of the method, the receiver receives the ATP confirmation signal prior, during or after implantation of the pacing device.

In one embodiment of the method, the receiver of the pacing device receives the ATP confirmation signal and/or the upgrade information for the ATP mode wirelessly or via a lead electrically connected to the pacing device.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The present invention will now be described in further detail with reference to the accompanying schematic drawings, in which.

DETAILED DESCRIPTION

Figure 1:
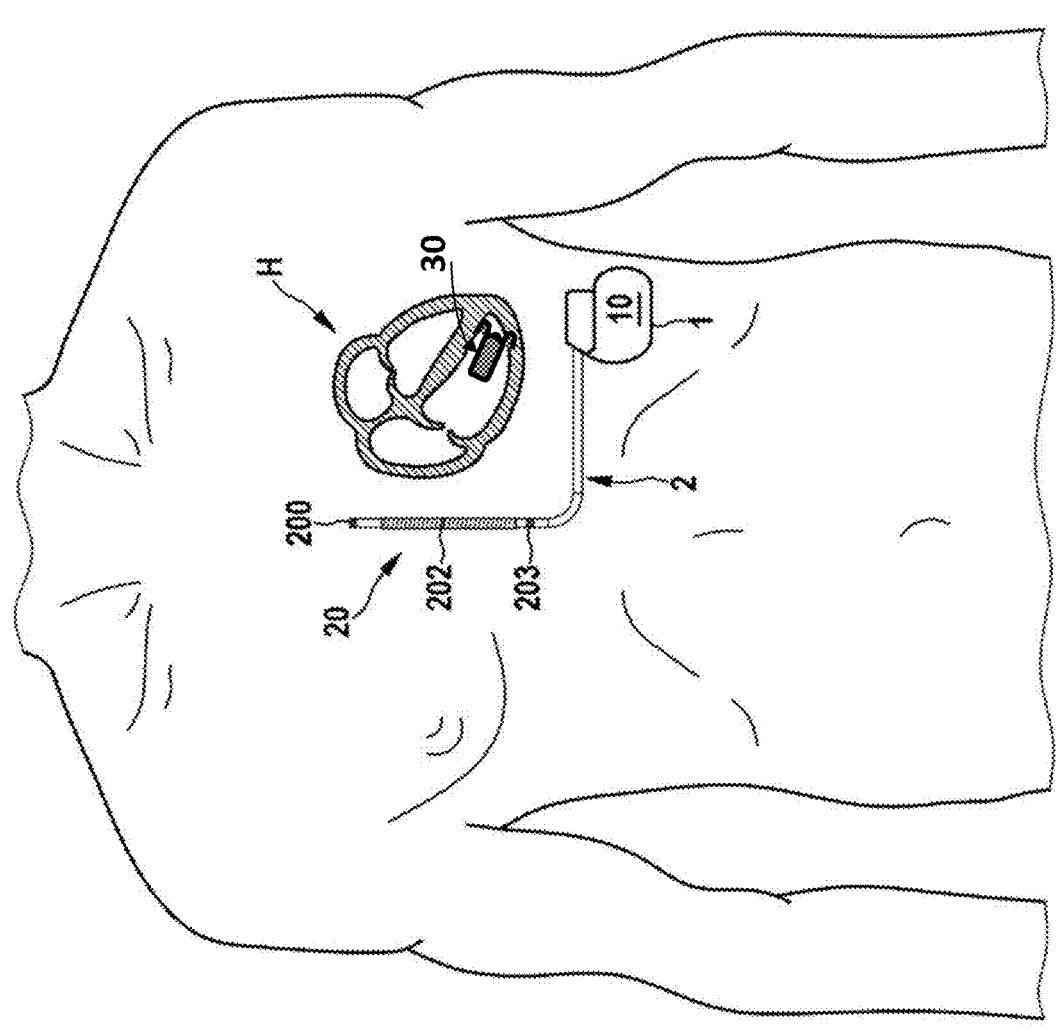
FIG. 1 shows an exemplary implantation of an inventive cardiac rhythm management system within a human patient's body.

FIG. 1 shows a first embodiment of a cardiac rhythm management system implanted in a human patient's body. The system comprises a subcutaneous implantable cardioverter defibrillator (S-ICD) 1 as a defibrillation device with a housing 10 and an electrode lead 2 connected to the housing 10. Further, the system comprises an implantable leadless pacemaker (ILP) 30 as a pacing device implanted within one, e.g., the right, ventricle of the heart H.

Figure 7:
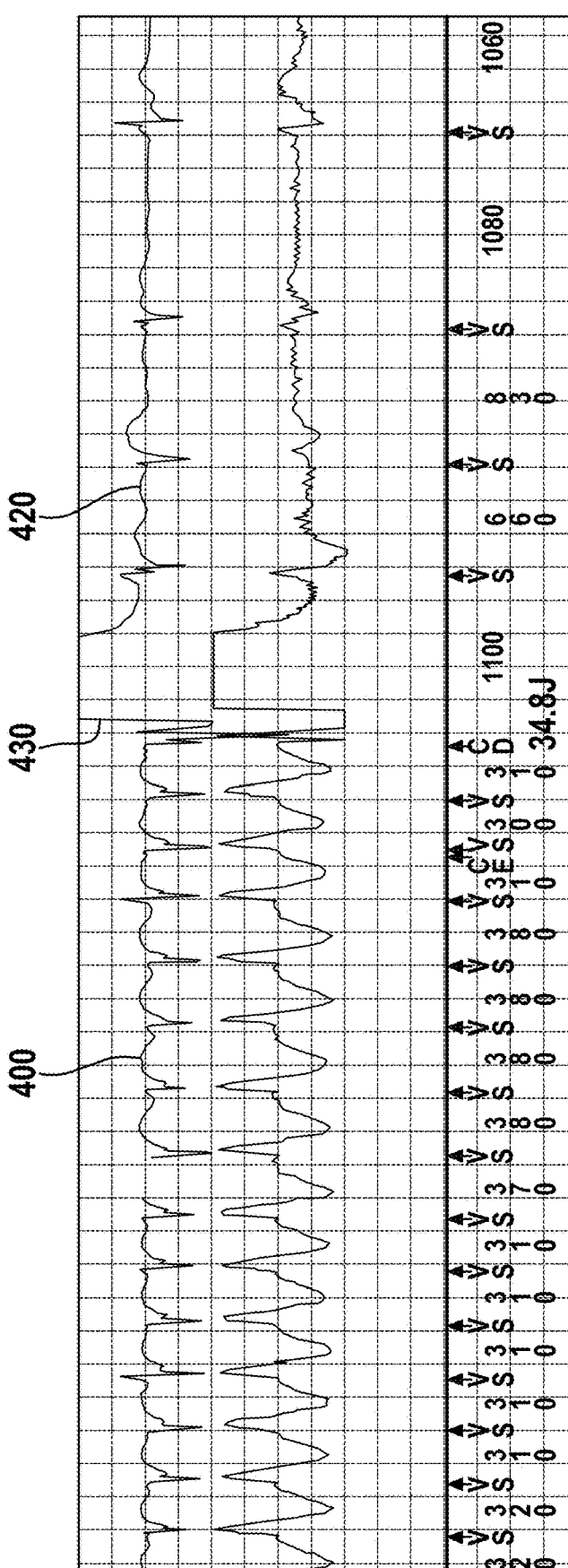
FIG. 7 shows an electrocardiogram containing a signal of a shock therapy.

The ILP 30 comprises one or more electrodes as a detection unit for sensing electric signals of the heart H. Further, the one more electrodes may be used for application of anti-tachycardia pacing (ATP) therapy or other cardiac therapy. The detected electric signals are transmitted to a processor accommodated within the ILP 30. The processor analyzes the electric signals of the heart (e.g., ECG signals) and thereby determines the patient's cardiac rhythm which may comprise, as shown in FIG. 7, a normal cardiac rhythm 420, a ventricular tachyarrhythmia 400 or a shock 430 provided by the S-ICD as an anti-tachycardia therapy. The processor is further adapted to generate and deliver signals for ATP therapy to the one or more electrodes of the ILP 30. The functions of the processor regarding the ATP therapy may be activatable by an operator, for example, via a communication link to an external control unit.

Figure 6:
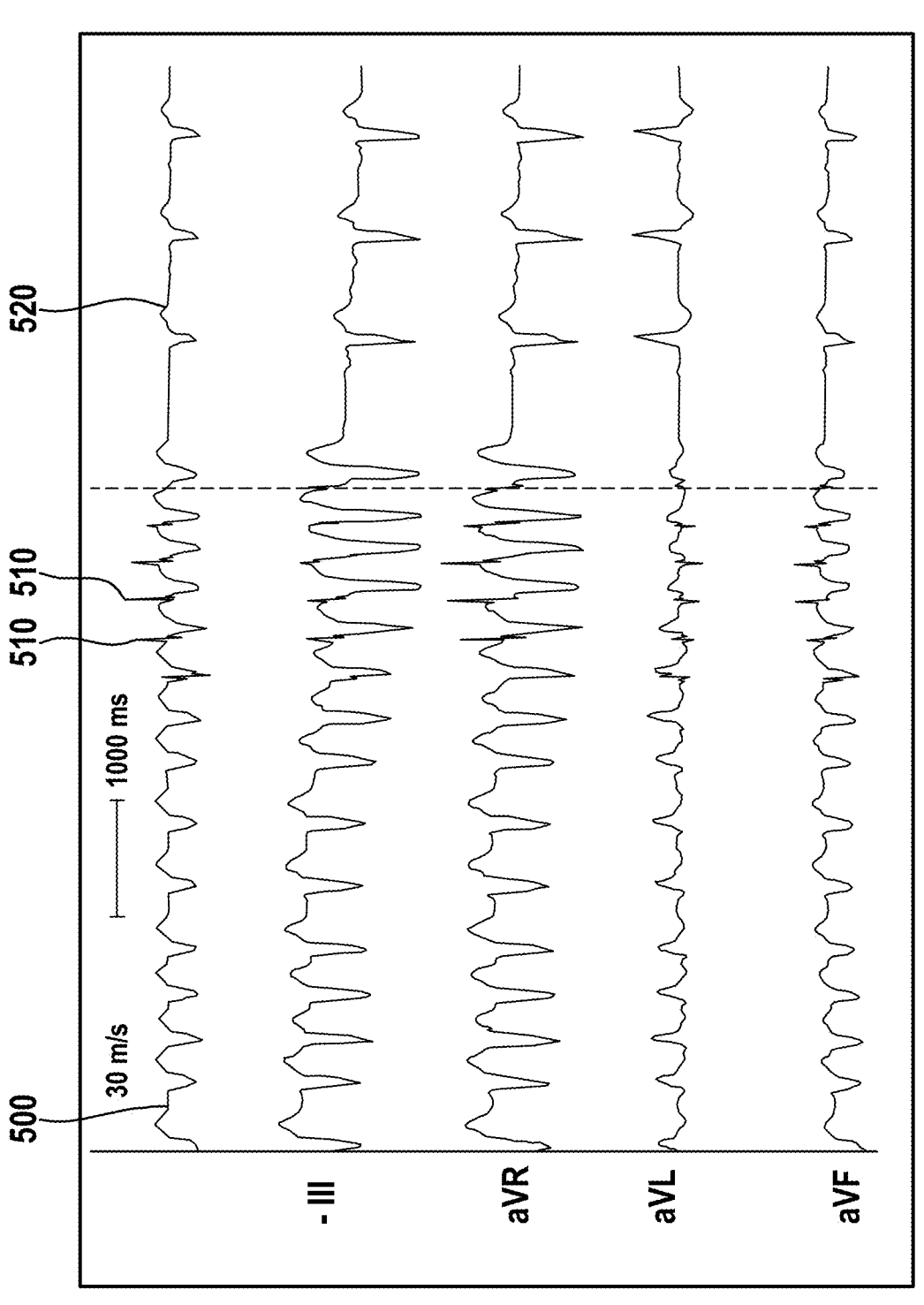
FIG. 6 shows an electrocardiogram containing signals of an antitachycardia pacing therapy.

The S-ICD 1 comprises within its housing 10 a second processor and a shock unit. The lead 2 is implanted subcutaneous along the sternum 20 and comprises two detection electrodes 200, 203 as a second detection unit and a shock coil 202 for application of a cardioversion or defibrillation shock. The detection electrodes 200, 203 detect electric signals of and around the heart H and transmit these signals to the second processor accommodated within the housing 10. The second processor analyzes the electric signals of the heart (e.g., the ECG signals) and thereby determines the patient's cardiac rhythm which may comprise, as shown in FIG. 6, a normal cardiac rhythm 520, a tachyarrhythmia 500 or ATP signals 510 provided by the ILP 30 as an anti-tachycardia therapy. The second processor is further adapted to generate and deliver signals transmitted to the shock unit which generates at least one cardioversion or defibrillation shock for anti-tachycardia therapy to shock coil 202. The shock unit has to run through a loading/charging time in which the necessary electric voltage is generated for the one or more shocks delivered by the shock coil 202 as shock therapy.

Figure 2:
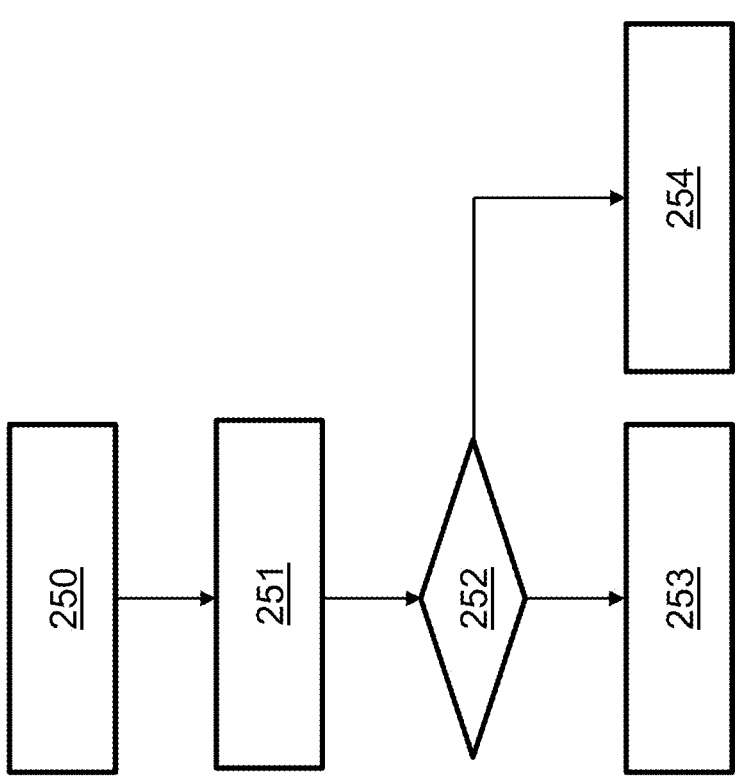
FIG. 2 depicts a flow chart of a first embodiment of an inventive method for operation of a pacing device.
Figure 3:
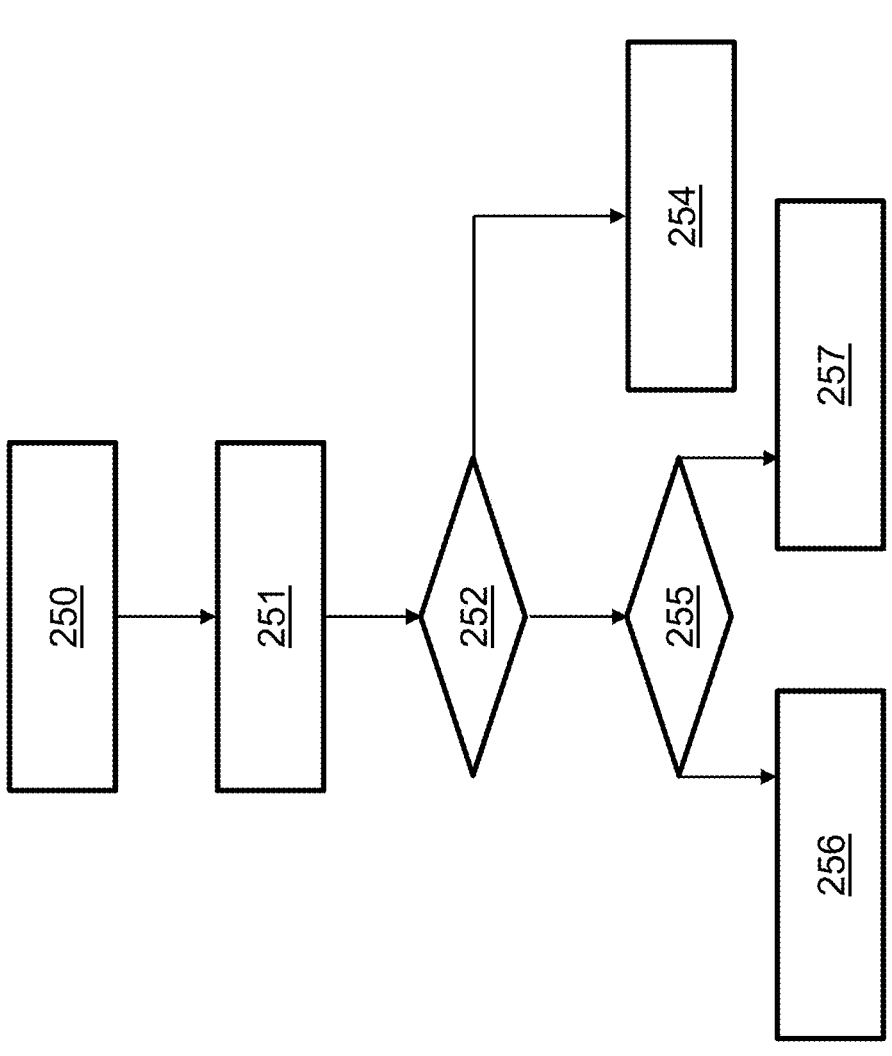
FIG. 3 depicts a flow chart of a second embodiment of an inventive method for operation of a pacing device.
Figures 4, 5:
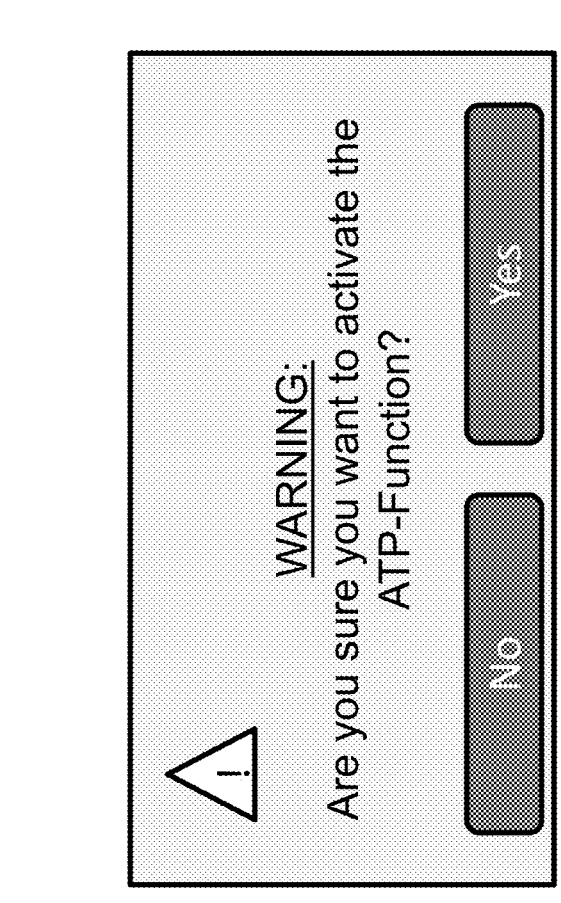
FIG. 4 shows an example of a warning notice according to step 251 of the flow charts of FIG. 2 or 3.
FIG. 5 shows an example of a warning notice according to step 255 of the flow chart of FIG. 3.

During initialization of the ILP after implantation an initial programming is performed (see step 250 in FIG. 2). Then, a warning notice is displayed (see step 251) at an external device communicatively connected to the ILP 30 which is shown in FIG. 4. In this warning notice the operator is informed that the ATP mode is only allowed to be activated if a defibrillator (e.g., the S-ICD 1) is implanted, as well. The warning notice shown in FIG. 4 further asks whether the defibrillation device is really implanted. Then, in step 252 the operator provides his/her response to the warning notice by selecting one of its boxes each of which containing one of the answers to the question indicated above. If the box "Yes" is chosen, the method continues with step 253 transmitting a predefined confirmation information to the receiver of the ILP 30 by a sender of the external device. As a result on that the processor of the ILP 30 activates its ATP mode. If the box "No" is chosen, the method continues with step 254 and terminates the method without activating the ATP mode of ILP 30. In an alternate embodiment shown in FIG. 3 after the box "Yes" is chosen in step 255 the external device displays a confirmation notice in order to confirm that now the ATP mode of ILP 30 is activated for the operator. An example of such confirmation notice is shown in FIG. 5. The operator may confirm its choice by clicking on the box "Yes" thereby providing the pre-defined confirmation information to the receiver of the ILP 30 (step 256). If the operator does not confirm his/her choice by choosing "No", the method continues with step 257 and terminates the method without activating the ATP mode. The second confirmation demanded from the operator makes sure that the operator intentionally provided his/her reaction to the warning notice. The warning notice may refer to additional information provided with one document accompanying the pacing device.

The above described pacing device, system and method allows variable usage of a pacing device individually or in cooperation with a defibrillation device, wherein the ATP mode is only activated and/or upgraded if a respective pre-defined confirmation information signal is received by the receiver of the pacing device.

Furthermore, the above described pacing device, system and method enhances patient safety with regard to a pacing device which is able to deliver ATP but no defibrillation shock, like for instance an ILP. A ventricular tachycardia is typically treated first with ATP. If multiple attempts of ATP are unsuccessful, a shock must be delivered as final action in order to terminate the life threatening tachycardia. If a pacing device is only capable of delivering ATP, it needs to be ensured that a shock therapy is available for the patient via another device, for instance an SICD. If the ATP function of a pacing device is activated without the possibility of an additional shock therapy, a ventricular tachycardia might not be treated sufficiently, putting the patient at risk. The present invention ensures that ATP needs to be activated in a pacing device by a confirmation signal transmitted by an external device or produced by operation of an actuator. The additional confirmation step provides additional safety in the usage of pacing devices with ATP function.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

REFERENCE NUMERALS

1 S-ICD
2 electrode lead
H heart
10 housing
20 sternum
30 ILP
200 detection electrode
202 shock coil
203 detection electrode
250 step of an inventive method for operation of a pacing device
251 step of an inventive method for operation of a pacing device
252 step of an inventive method for operation of a pacing device
253 step of an inventive method for operation of a pacing device
254 step of an inventive method for operation of a pacing device
255 step of an inventive method for operation of a pacing device
256 step of an inventive method for operation of a pacing device
257 step of an inventive method for operation of a pacing device
400 tachyarrhythmia
410 ATP therapy
420 normal cardiac rhythm
430 shock therapy
500 tachyarrhythmia
510 ATP signal
520 normal cardiac rhythm

The invention claimed is:

1. An implantable pacing device, including an implantable leadless pacemaker, with a housing, wherein the pacing device comprises a processor and a receiver electrically connected to the processor or integrated therein, wherein the processor is adapted to deliver signals for electric stimulation of a patient's heart according to at least one first stimulation mode and deliver signals for electric stimulation of the patient's heart according to an antitachycardiac pacing mode (ATP mode), wherein the ATP mode is initially deactivated, wherein the receiver is adapted to receive, on the occasion of an initial programming of the implantable pacing device and/or on the occasion of a pre-defined service date, an ATP confirmation signal transmitted by an external device or produced by operation of an actuator accommodated at the housing of the pacing device, wherein the processor is adapted to activate the ATP mode only if the ATP confirmation signal comprises a pre-defined confirmation information, and wherein the pacing device further comprises a transmitter, wherein the processor is adapted to provide pre-defined warning information data comprising warning information about the usage of the ATP mode, wherein the transmitter is adapted to transmit the warning information data to an external device.

2. The pacing device according to claim 1, wherein the receiver is adapted to receive the ATP confirmation signal prior, during or after implantation of the pacing device.

3. The pacing device according to claim 1, wherein the pre-defined confirmation information comprises at least one parameter of an additional antitachycardia device type, including a defibrillator type, wherein the pacing device and the additional antitachycardia device are adapted to be implanted into the same patient.

4. The pacing device according to claim 1, wherein the receiver of the pacing device is adapted to receive the ATP confirmation signal for the ATP mode wirelessly or via a lead electrically connected to the pacing device.

5. The pacing device according to claim 1, wherein the processor is adapted to apply at least one criterion for ventricular/supraventricular tachycardia discrimination with regard to a cardiac rhythm detected by a detection unit of the pacing device.

6. The pacing device according to claim 1, wherein the ATP mode comprises at least two different antitachycardia pacing pattern elements usable during electric stimulation of the patient's heart according to the ATP mode.

7. The pacing device according to claim 6, wherein a first antitachycardia pacing pattern element comprises at least one burst and/or a second antitachycardia pacing pattern element comprises at least one ramp and/or a third antitachycardia pacing pattern element comprises at least one burst in combination with an extra stimulus.

8. A heart treatment system comprising the pacing device of claim 1 and an additional antitachycardia device, including a subcutaneous implantable cardioverter defibrillator (S-ICD 1).

9. A method for operation of an implantable pacing device, including an implantable leadless pacemaker, with a housing, wherein the pacing device comprises a processor and a receiver electrically connected to the processor or integrated therein, wherein the processor is adapted to deliver signals for electric stimulation of a patient's heart according to at least one first stimulation mode and is adapted to deliver signals for electric stimulation of the patient's heart according to an antitachycardiac pacing mode (ATP mode), wherein the ATP mode is initially deactivated, wherein the receiver receives, on the occasion of an initial programming of the implantable pacing device and/or on the occasion of a pre-defined service date, an ATP confirmation signal transmitted by an external device or by produced by operation of an actuator accommodated at the housing of the pacing device, wherein the processor activates the ATP mode only if the received ATP confirmation signal comprises a pre-defined confirmation information, and wherein the pacing device further comprises a transmitter, wherein the processor is adapted to provide pre-defined warning information data comprising warning information about the usage of the ATP mode, wherein the transmitter transmits the warning information data to an external device.

10. The method according to claim 9, wherein the receiver receives the ATP confirmation signal prior, during or after implantation of the pacing device.

11. The method according to claim 9, wherein the receiver of the pacing device receives the ATP confirmation signal for the ATP mode wirelessly or via a lead electrically connected to the pacing device.

12. The method according to claim 9, wherein the processor applies at least one criterion for ventricular/supraventricular tachycardia discrimination with regard to a cardiac rhythm detected by a detection unit of the pacing device.

13. The method according to claim 9, wherein during electric stimulation of the patient's heart according to the ATP mode at least two different antitachycardia pacing patterns are used.

14. An implantable pacing device, including an implantable leadless pacemaker, with a housing, wherein the pacing device comprises a processor and a receiver electrically connected to the processor or integrated therein, wherein the processor is adapted to deliver signals for electric stimulation of a patient's heart according to at least one first stimulation mode and deliver signals for electric stimulation of the patient's heart according to an antitachycardiac pacing mode (ATP mode), wherein the ATP mode is initially deactivated, wherein the receiver is adapted to receive, on the occasion of an initial programming of the implantable pacing device and/or on the occasion of a pre-defined service date, an ATP confirmation signal transmitted by an external device or produced by operation of an actuator accommodated at the housing of the pacing device, wherein the processor is adapted to activate the ATP mode only if the ATP confirmation signal comprises a pre-defined confirmation information, and wherein the pre-defined confirmation information comprises at least one parameter of an additional antitachycardia device type, including a defibrillator type, wherein the pacing device and the additional antitachycardia device are adapted to be implanted into the same patient.

* * * * *